(12) United States Patent
Katsuki et al.

(10) Patent No.: US 10,391,224 B2
(45) Date of Patent: Aug. 27, 2019

(54) PRESSURE SENSING EXTRACORPOREAL CIRCULATION DEVICE

(71) Applicant: TERUMO KABUSHIKI KAISHA, Tokyo (JP)

(72) Inventors: Ryohei Katsuki, Kanagawa (JP); Tomoki Utsugida, Kanagawa (JP); Yuuki Hara, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 275 days.

(21) Appl. No.: 15/605,067

(22) Filed: May 25, 2017

(65) Prior Publication Data

US 2017/0258980 A1 Sep. 14, 2017

Related U.S. Application Data

(63) Continuation of application No. PCT/JP2015/074478, filed on Aug. 28, 2015.

(30) Foreign Application Priority Data

Dec. 12, 2014 (JP) ................. 2014-252014

(51) Int. Cl.
*A61M 1/36* (2006.01)
*A61M 1/10* (2006.01)
*A61M 1/16* (2006.01)

(52) U.S. Cl.
CPC .......... *A61M 1/3607* (2014.02); *A61M 1/101* (2013.01); *A61M 1/1006* (2014.02);
(Continued)

(58) Field of Classification Search
CPC .. A61M 1/1006; A61M 1/101; A61M 1/1086; A61M 1/1698; A61M 1/3607;
(Continued)

(56) References Cited

U.S. PATENT DOCUMENTS

| 6,142,752 A | 11/2000 | Akamatsu et al. |
| 8,452,250 B2 | 5/2013 | Ishikawa et al. |
| 2012/0143115 A1 | 6/2012 | Muller-Spanka et al. |

FOREIGN PATENT DOCUMENTS

| JP | 08-238310 A | 9/1996 |
| JP | 201150687 A | 3/2011 |

(Continued)

OTHER PUBLICATIONS

European Search and Opinion Report, PCT/JP2015074478, dated May 25, 2018.
(Continued)

*Primary Examiner* — Leslie R Deak
(74) *Attorney, Agent, or Firm* — MacMillan, Sobanski & Todd, LLC (57) ABSTRACT

An extracorporeal blood circulation system reduces the risk of generation of air bubbles entering the circulation circuit associated with placement of a pressure sensor that detects a patient's blood pressure at a blood removal line. Instead of directly measuring pressure at the blood removal line where suction exists, an intermediate part pressure sensor detects pressure between a centrifugal pump and an oxygenator. A controller identifies a discharge pressure specific to the centrifugal pump based on a rotation speed of the pump and a blood flow rate. The discharge pressure and the intermediate pressure values are combined to estimate the pressure at the blood removal line.

6 Claims, 6 Drawing Sheets

(52) U.S. Cl.
CPC ........ *A61M 1/1086* (2013.01); *A61M 1/1698* (2013.01); *A61M 1/36* (2013.01); *A61M 1/3666* (2013.01); *A61M 2205/3331* (2013.01); *A61M 2205/3334* (2013.01); *A61M 2205/3355* (2013.01); *A61M 2230/207* (2013.01); *A61M 2230/50* (2013.01)

(58) Field of Classification Search
CPC ........ A61M 1/3666; A61M 2205/3331; A61M 2205/3334; A61M 2205/3355; A61M 2230/207; A61M 2230/50
See application file for complete search history.

(56) References Cited

FOREIGN PATENT DOCUMENTS

| | | |
|---|---|---|
| JP | 2011045450 A | 10/2011 |
| JP | 2013192712 A | 9/2013 |
| JP | 201468739 A | 4/2014 |
| WO | 9814228 | 4/1998 |

OTHER PUBLICATIONS

JPO Office Action dated May 28, 2019, for related Divisional JP2018-037759.

PRESSURE SENSING EXTRACORPOREAL CIRCULATION DEVICE

CROSS REFERENCE TO RELATED APPLICATIONS

This application is a continuation of PCT Application No. PCT/JP2015/074478, filed Aug. 28, 2015, based on and claiming priority to Japanese application no. 2014-252014, filed Dec. 12, 2014, both of which are incorporated herein by reference in their entirety.

TECHNICAL FIELD

The present invention relates to an extracorporeal circulation system capable of measuring a blood pressure within an extracorporeal circulation circuit.

BACKGROUND ART

Conventionally, in the case of performing a cardiac surgery operation of a patient or supporting the cardiopulmonary function, or the like, extracorporeal blood circulation is carried out in which a blood pump of an extracorporeal circulation system is actuated to withdraw blood through a blood removal line (blood removal tube) connected to a vein of the patient so that a gas exchange in the blood is carried out in an oxygenator disposed downstream relative to the blood pump and then this blood is returned to an artery of the patient again through a blood sending line (blood sending tube).

Regarding such an extracorporeal circulation system in which the blood flows in order of the blood removal line, the blood pump, the oxygenator, and the blood sending line, a pressure sensor is conventionally connected to the blood removal line close to the venous side of the patient (see, e.g., Japanese Patent Laid-open No. 2013-192712). Due to this, the blood pressure state of the patient can be determined more correctly. Specifically, for example, it can be envisaged that the amount of blood in the body of the patient is insufficient if the value of the pressure in the tube of the blood removal line is excessively low.

To connect the pressure sensor to the blood removal line as above, generally a method is employed in which a three-way stopcock is connected to the blood removal tube and the pressure sensor is fitted to a connector of this three-way stopcock. Furthermore, in recent years, a device of a type in which a pressure sensor is built into a tube in advance has also existed (see, e.g., Japanese Patent Laid-open No. 2014-68739).

SUMMARY OF INVENTION

Technical Problems

Because the blood removal line is disposed on the upstream or inlet side of the blood pump, a negative pressure (i.e., suction) state is made in the tube. For this reason, in the case of connecting a pressure sensor by using a three-way stopcock, there is a possibility that air could be drawn into the tube, resulting in generation of an air bubble if the connection to the three-way stopcock is loose or a user forgets to close the stopcock when removing the pressure sensor. Note that with the device of the type in which a pressure sensor is connected to a tube in advance, the structure is complicated and the manufacturing cost is high although the risk of drawing of air is low. In addition, there is also a problem that sterilization is difficult.

The present invention provides an extracorporeal circulation system in which the risk of generation of an air bubble is alleviated and the state of a patient is also easily determined.

Technical Solution

The aforesaid problems are solved by an extracorporeal circulation system including a blood removal line through which blood withdrawn from a body of a subject is conveyed, a centrifugal pump that is connected downstream of the blood removal line and carries out blood sending by rotational motion, an oxygenator connected downstream relative to the centrifugal pump, a blood return line that is downstream relative to the oxygenator and returns blood to the inside of the body, and a flow rate sensor that detects a blood flow rate in the blood return line. The extracorporeal circulation device includes an intermediate part pressure sensor that detects pressure of the conveyed blood between the centrifugal pump and the oxygenator, and a discharge pressure determining unit that identifies discharge pressure specific to the centrifugal pump based on the rotation speed of the centrifugal pump and the blood flow rate detected in the flow rate sensor.

In the configuration of the aforesaid present invention, the pressure sensor for measuring the pressure in the circuit is disposed not on the blood removal line, which becomes a negative (i.e., suction) pressure state, but between the centrifugal pump and the oxygenator, i.e. in the circuit that is immediately downstream of the centrifugal pump and is in a high positive pressure state. For this reason, even when the pressure sensor is connected by a three-way stopcock, the risk that air bubbles could be drawn from the position of the three-way stopcock is low. Therefore, air can be effectively prevented from entering the inside of the circulation circuit. Furthermore, a tube between the centrifugal pump and the oxygenator is short and thus pressure change resulting from the deformation of the tube is also small. Therefore, fluctuation in the pressure value measured in the intermediate part pressure sensor is also small and the user also is unlikely to be forced to make an unnecessary determination. In addition, when the pressure sensor is provided between the centrifugal pump and the oxygenator so that pressure is measured downstream of the oxygenator, the pressure loss in the oxygenator can be estimated through subtraction of the pre-oxygenator pressure from the post-oxygenator pressure. Due to this, it is also possible to grasp the deterioration of the oxygenator and so forth. Moreover, in the configuration of the aforesaid present invention, the extracorporeal circulation system has the discharge pressure determining unit that identifies the discharge pressure specific to the centrifugal pump based on the rotation speed of the centrifugal pump and the blood flow rate detected in the flow rate sensor in the blood sending line. For this reason, it can be detected that the state of the patient is abnormal whenever the pressure measured in the intermediate part pressure sensor (i.e., the pressure sensor existing immediately subsequent to the centrifugal pump) is an abnormal numerical value that is inconsistent with the expected discharge pressure specific to the centrifugal pump used (for example, if the pressure measured in the intermediate part pressure sensor is lower than even 300 mmHg although the discharge pressure specific to the centrifugal pump is 600 mmHg when operating at the set rotation speed of the centrifugal pump, then the pressure from the venous side of the patient is too low and thus it can be concluded that the amount of blood in the body of the patient is too small).

Furthermore, and most preferably, the extracorporeal circulation system is characterized by including a blood removal pressure calculating unit that subtracts the discharge pressure identified in the discharge pressure determining unit from the pressure measured by the intermediate part pressure sensor to estimate pressure in the blood removal line. Therefore, the pressure in the tube in the blood removal line is estimated, which makes it easier to automatically detect the blood removal state of the patient. That is, it can be predicted that the pressure obtained by subtracting the specific discharge pressure value (as identified in the discharge pressure determining unit) from the pressure measured by the intermediate part pressure sensor is not less than the actual pressure in the blood removal line (regardless of the discharge pressure of the centrifugal pump). Therefore, although a pressure sensor is not provided in the blood removal line, the pressure in the blood removal line can still be reliably obtained.

Moreover, preferably, the extracorporeal circulation system is characterized by including a blood removal state determining unit that determines whether or not the pressure calculated in the blood removal pressure calculating unit has surpassed a threshold composed of a value necessary for determining blood removal failure, and informing means that informs a user of the result obtained by the blood removal state determining unit. Therefore, the user can be notified of a blood removal failure by the informing means and can promptly examine potential reasons for the lowering of the amount of blood of the subject, such as improper insertion of a cannula, or the like.

Furthermore, preferably, the extracorporeal circulation device is characterized in that the blood removal state determining unit carries out the determination only after a required time which allows the discharge pressure of the centrifugal pump to become stable after the rotation speed of the centrifugal pump is set (e.g., changed). Therefore, even if the discharge pressure of the centrifugal pump is briefly unstable after an initial starting actuation of the centrifugal pump or after a change between two different rotation speeds, the needless informing of the informing means can be prevented.

Moreover, preferably, the extracorporeal circulation device is characterized in that the blood removal state determining unit determines whether or not an average value of the pressure calculated in the blood removal pressure calculating unit has surpassed the threshold, or determines whether or not the pressure calculated in the blood removal pressure calculating unit has consecutively surpassed the threshold or consecutively fallen below the threshold. Therefore, even if the case in which the pressure calculated in the blood removal pressure calculating unit falls below the required threshold instantaneously exists in a time period in which the discharge pressure of the centrifugal pump should be stable, a needless informing of the informing means can be effectively prevented.

Furthermore, preferably, the extracorporeal circulation device is characterized in that the discharge pressure is identified while taking account of a hematocrit value and/or a blood temperature. Thus, the blood removal pressure calculating unit can estimate the pressure in the blood removal line with higher accuracy because it accounts for the fact that the hematocrit value and the blood temperature change the viscosity of the blood, which affects the discharge pressure.

Advantageous Effects

As above, according to the present invention, an extracorporeal circulation device with which the risk of generation of an air bubble is alleviated and the blood removal state of a patient is also easily determined can be provided.

MODE FOR CARRYING OUT THE INVENTION

A preferred embodiment of the present invention will be described in detail below with reference to the drawings. The embodiment to be described below is a preferred concrete example of the present invention and therefore is given various qualifications that are technically preferable. However, the scope of the present invention is not limited to these aspects unless there is a particular description of limiting the present invention in the following explanation. Furthermore, in the following drawings, a place given the same symbol has the same configuration unless there is particular reference.

(Outline of Extracorporeal Circulation Device and Characteristics Thereof)

An extracorporeal circulation device of the present embodiment is used in the case of "extracorporeal membrane oxygenation" and "cardiopulmonary bypass" for example. The "cardiopulmonary bypass" is carrying out circulation operation of blood and gas exchange operation (oxygen addition and/or carbon dioxide removal) for this blood by the extracorporeal circulation device in the case in which the blood circulation in the heart is temporarily stopped due to a surgery operation for example. The "extracorporeal membrane oxygenation" is carrying out support of circulation operation of blood by the extracorporeal circulation device in the case in which the heart of a patient cannot fulfill the sufficient function or in the state in which gas exchange by the lung cannot be sufficiently carried out. Some devices have a function of carrying out gas exchange operation for blood.

Figure 1:
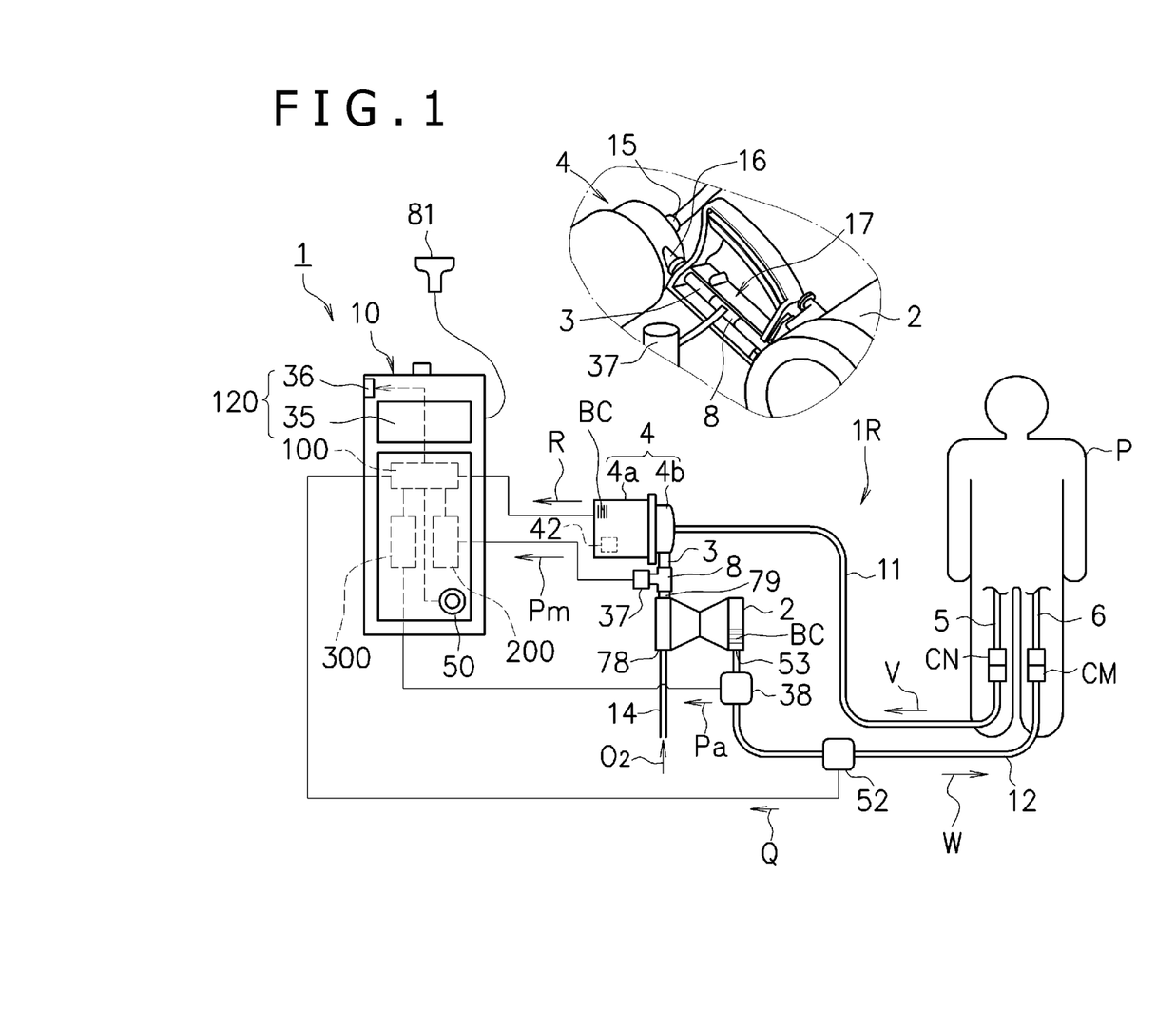
FIG. 1 is a system diagram showing a preferred embodiment of an extracorporeal circulation device of the present invention.

FIG. 1 is a systematic diagram of an extracorporeal circulation device 1 according to the embodiment of the present invention. Note that a diagram surrounded by a one-dot-chain line is an enlarged view around an interlock tube 3 that couples a centrifugal pump 4 and an oxygenator 2. The extracorporeal circulation device 1 of this diagram has a blood circuit (referred to also as "blood circulation circuit") 1R including conduits of blood with which blood is removed from a vein of a patient (subject) P and thereafter this blood is returned to an artery of the patient again. The blood circuit 1R comprises (in order from blood removal to blood return to the inside of the body of the patient P), a blood-removal-side cannula 5, a blood removal line (blood removal tube) 11, centrifugal pump 4 that pumps blood, oxygenator 2 that carries out gas exchange operation for the blood, a blood sending line (blood sending tube) 12, and a blood-sending-side cannula 6. The blood circuit 1R substitutes for the heart and the lung.

The blood-removal-side cannula 5 is inserted in a vein of the patient P and is joined to the blood removal line 11 by a connector CN. Furthermore, the blood-sending-side cannula 6 is inserted in an artery of the patient P and is joined to the blood sending line 12 by a connector CM. The blood removal line 11 and the blood sending line 12 are conduits outside the body, and tubes made of a synthetic resin having high transparency, such as a vinyl chloride resin or silicone rubber, can be used for example. In the blood removal line 11, blood flows in a V-direction (toward the centrifugal pump 4). In the blood sending line 12, blood flows in a W-direction (toward the patient P).

The centrifugal pump 4 is connected to the downstream-side end part of the blood removal line 11, and withdraws blood from the vein of the patient P to remove the blood through the blood removal tube 11 when being actuated based on a command from a controller 10. Then, the removed blood can be sent to the artery of the patient P through the blood sending tube 12 after passing through the oxygenator 2. For example, the centrifugal pump 4 is composed of a pump head 4b having a rotor (not shown) in which a magnet is embedded and a drive motor (drive source) 4a to which a magnet is attached on the side of this pump head 4b. When the drive motor 4a rotates, the rotor rotates by a magnetic force. When the rotor rotates, blood that flows into the pump from an inflow port 15 existing at the central part of the pump is discharged from an outflow port 16 formed in the outer circumferential surface by a centrifugal force. The rotation speed of the drive motor 4a is set by an operation unit 50 formed of a rotary knob or the like of the controller 10 and is capable of rotation at 1000 to 5000 rpm for example (in the case of the present embodiment, at most 3000 rpm).

The centrifugal pump 4 of the present embodiment has rotation speed measuring equipment 42 such as an optical rotary encoder for example in the chassis of the drive motor 4a and rotation speed R of the drive motor 4a is detected. This detected rotation speed R is converted to an electrical signal and is transmitted to the controller 10, which enables the rotation speed of the centrifugal pump 4 to be grasped in real time. Furthermore, a publicly-available temperature sensor (not shown) is provided in the chassis of the pump head 4b and the detection result of this temperature sensor is transmitted to the controller 10, which enables measurement of the blood temperature. Moreover, electrical current change of the drive motor 4a is also transmitted to the controller 10 and thereby the controller 10 calculates the blood viscosity and measures the hematocrit value (for example, refer to Japanese Patent Laid-open No. 1999-76394). Note that the measurement means for the rotation speed R of the centrifugal pump 4, the blood temperature, and the hematocrit value are not limited to the above-described aspect and it is also possible to use another publicly-known means. In addition, on the centrifugal pump 4, a barcode BC for identification of the kind the centrifugal pump 4 is displayed. This barcode BC is read by a barcode reader 81 connected to the controller 10, which enables identification of the kind of the centrifugal pump 4 used.

The oxygenator 2 is a publicly-known membrane oxygenator disposed between the centrifugal pump 4 and the blood sending tube 12, and preferably a hollow fiber oxygenator, and more preferably an oxygenator of the external reflux type is used. Specifically, the oxygenator 2 of the present embodiment is supplied with a mixed gas in which the oxygen concentration is adjusted from a gas port 78 through a tube 14. The mixed gas that has entered from this gas port 78 passes in plural hollow fibers (gas exchange membranes of the hollow fiber type) obtained by setting porous membranes to a straw shape. In contrast, the blood that flows from the centrifugal pump 4 is introduced into the oxygenator 2 from a blood inflow port 79 different from the gas port 78. The blood that has entered from this blood inflow port 79 passes among the plural hollow fibers and is sent to the blood sending line 12 through an outflow port 53. Then, gas exchange is carried out between the inside and outside of the hollow fibers. Furthermore, a barcode BC for identification of the kind is displayed on the oxygenator 2 similarly to the centrifugal pump 4 and is read by the barcode reader 81, which enables identification of the kind. Note that the oxygenator 2 of the present invention is not limited to such an external reflux type and may be an internal reflux type or may be a membrane oxygenator different from the hollow fiber type.

In an intermediate section (i.e., the middle) of the blood sending line 12 downstream relative to the oxygenator 2, a blood-sending-side pressure sensor 38 that detects the pressure of the inside of the blood sending line 12 and a flow rate sensor 52 that detects the flow rate of the blood in the blood sending line 12 are disposed. The detection results of the blood-sending-side pressure sensor 38 and the flow rate sensor 52 are converted to an electrical signal and are transmitted to the controller 10. It is preferable for the blood-sending-side pressure sensor 38 to be disposed close to the outflow port 53 of the oxygenator 2, and the blood-sending-side pressure sensor 38 has a function of detecting the pressure as immediately after outflow from the oxygenator 2 as possible and measuring a post-oxygenator pressure to be described later. A publicly-known pressure meter can be used as the blood-sending-side pressure sensor 38. To cite one example, a pressure meter in which a pressure-sensitive element detects the displacement of a diaphragm due to the pressure and the displacement is converted to an electrical signal can be used.

The flow rate sensor 52 allows determination of the flow rate of blood that flows in the blood circuit 1R and is used herein to support a function of calculating the discharge pressure specific to the centrifugal pump 4, and so forth, as described later. A known flowmeter can be used as the flow rate sensor 52. In the case of the present embodiment, a sensor of an ultrasonic propagation time difference system is used. This sensor of the ultrasonic propagation time difference system transmits and receives ultrasonic waves regarding both of the bloodstream direction W and the opposite direction thereof and detects the blood flow rate from the difference in the transmission time of the ultrasonic waves based on these directions. The flow rate sensor 52 in FIG. 1 is disposed separately from the blood-sending-side pressure sensor 38 and is disposed downstream relative to the blood-sending-side pressure sensor 38. The blood-sending-side pressure sensor 38 and the flow rate sensor 52 disposed on the blood sending line 12 in the present invention are not limited to such an aspect. One detector may double as a blood-sending-side pressure sensor and a flow rate sensor and the pressure and the blood flow rate in the blood sending line 12 may be measured at one place.

Moreover, the extracorporeal circulation device 1 of the present embodiment has an intermediate part pressure sensor 37 that is a pressure sensor that detects the pressure in the circuit between the centrifugal pump 4 and the oxygenator 2. This intermediate part pressure sensor 37 has two functions in combination mainly. Although details will be described later, one is a function for estimating the pressure in the blood removal line 11 and the other is a function for determining the replacement timing of the oxygenator 2. Regarding the intermediate part pressure sensor 37, the sensor itself is a publicly-known sensor and may be the same as or different from the blood-sending-side pressure sensor 38. Furthermore, a publicly-known method can also be used as the method for attaching the intermediate part pressure sensor 37 to the interlock tube 3 between the centrifugal pump 4 and the oxygenator 2. In the present embodiment, as one example of the method, the intermediate part pressure sensor 37 is directly or indirectly connected to a connector of a three-way stopcock 8 connected to the interlock tube 3. Note that the interlock tube 3 is formed to be short compared with at least the tubes of the blood removal line 11 and the blood sending line 12 so that the pressure loss between the centrifugal pump 4 and the oxygenator 2 may be as small as possible. Preferably, the interlock tube 3 passes in a guard member 17 that guards the periphery of the interlock tube 3. The guard member 17 engages with both end parts of the interlock tube 3 while keeping the interlock tube 3 straight. This prevents bending and so forth of the interlock tube 3. Furthermore, the intermediate part pressure sensor 37 (in the diagram, the three-way stopcock 8 for connecting to the interlock tube 3) is connected adjacent to the interlock tube 3 in this guard member 17, more preferably close to the centrifugal pump 4.

The centrifugal pump 4, the blood-sending-side pressure sensor 38, the flow rate sensor 52, and the intermediate part pressure sensor 37 like the above ones are connected to the controller 10 and transmission and reception of signals are carried out between these components and the controller 10. The controller 10 is a dedicated computer composed of a central processing unit (CPU), a read only memory (ROM), a random access memory (RAM), and so forth that are connected to each other via a bus, which is not diagrammatically represented, and are configured to operate on the basis of a clock signal of a clock transmitter. However, the controller 10 may be a computer having general versatility. The controller 10 has a main control unit 100 that carries out determination and control of the overall operation, a control unit 200 for blood-removal-side monitoring that mainly carries out determination and control relating to the blood removal line 11, and a control unit 300 for oxygenator monitoring that mainly carries out determination and control relating to the oxygenator. The control unit of the present invention is not limited to such a configuration. The control unit 200 for blood-removal-side monitoring and the control unit 300 for oxygenator monitoring may be combined into the main control unit 100 and be united, and operation and control of the device may be carried out in accordance with a predetermined procedure.

The operation unit 50 formed of a rotary knob or the like is connected to the main control unit 100 and a signal based on operation of this operation unit 50 is distributed to the respective units. For example, this signal is transmitted to the drive motor 4a connected to the main control unit 100, which enables the rotation speed of the centrifugal pump 4 to be set by manual operation of the operation unit 50. Furthermore, the rotation speed measuring equipment 42, the flow rate sensor 52, the control unit 200 for blood-removal-side monitoring, and the control unit 300 for oxygenator monitoring are connected to the main control unit 100, and the detection results of the rotation speed measuring equipment 42 and the flow rate sensor 52 are distribution-transmitted to the control unit 200 for blood-removal-side monitoring and the control unit 300 for oxygenator monitoring as signals in accordance with a predetermined procedure. Furthermore, an informing unit 120 composed of an alarm 36 such as a buzzer or a speaker and a display screen 35 such as a liquid crystal screen is connected to the main control unit 100. Based on signals received from the respective control units 200 and 300, the flow rate sensor 52, and so forth, the informing unit 120 can inform the contents of the signals. The alarm 36 is configured to make warning or the like for informing an abnormality in the pressure value of the blood removal line 11 or informing the replacement timing of the oxygenator 2 as described later. On the display screen 35, information regarding the operation unit 50 and so forth (setting of the rotation speed of the centrifugal pump 4, the kinds of centrifugal pump 4 and oxygenator 2, required threshold, and so forth) and various kinds of messages (blood flow rate, hematocrit value, blood temperature, values of pressure in the blood removal line 11 and the blood sending line 12, contents of an alarm, and so forth) are displayed.

The control unit 200 for blood-removal-side monitoring is a control unit for mainly determining the pressure in the blood removal line 11 and monitoring the blood removal state based on the intermediate part pressure sensor 37 electrically connected to the control unit 200 and the respective circuits or programs even though a pressure sensor is not attached to the blood removal line 11. The determination and control method for monitoring this blood removal state will be described in detail with reference to FIG. 2 and subsequent drawings.

The control unit 300 for oxygenator monitoring is a control unit for estimating the pressure loss in the oxygenator 2 by subtracting a pressure value Pm measured in the intermediate part pressure sensor 37 (pressure value of the upstream side relative to the oxygenator 2) from a pressure value Pa measured in the blood-sending-side pressure sensor 38 (pressure value of the downstream side relative to the oxygenator 2) in connection with the function of determining the replacement timing of the oxygenator 2 based on this pressure loss. The determination and control method relating to this monitoring of the oxygenator 2 will also be described in detail with reference to FIG. 2 and subsequent drawings.

[System Configuration of Extracorporeal Circulation Device]

Figure 2:
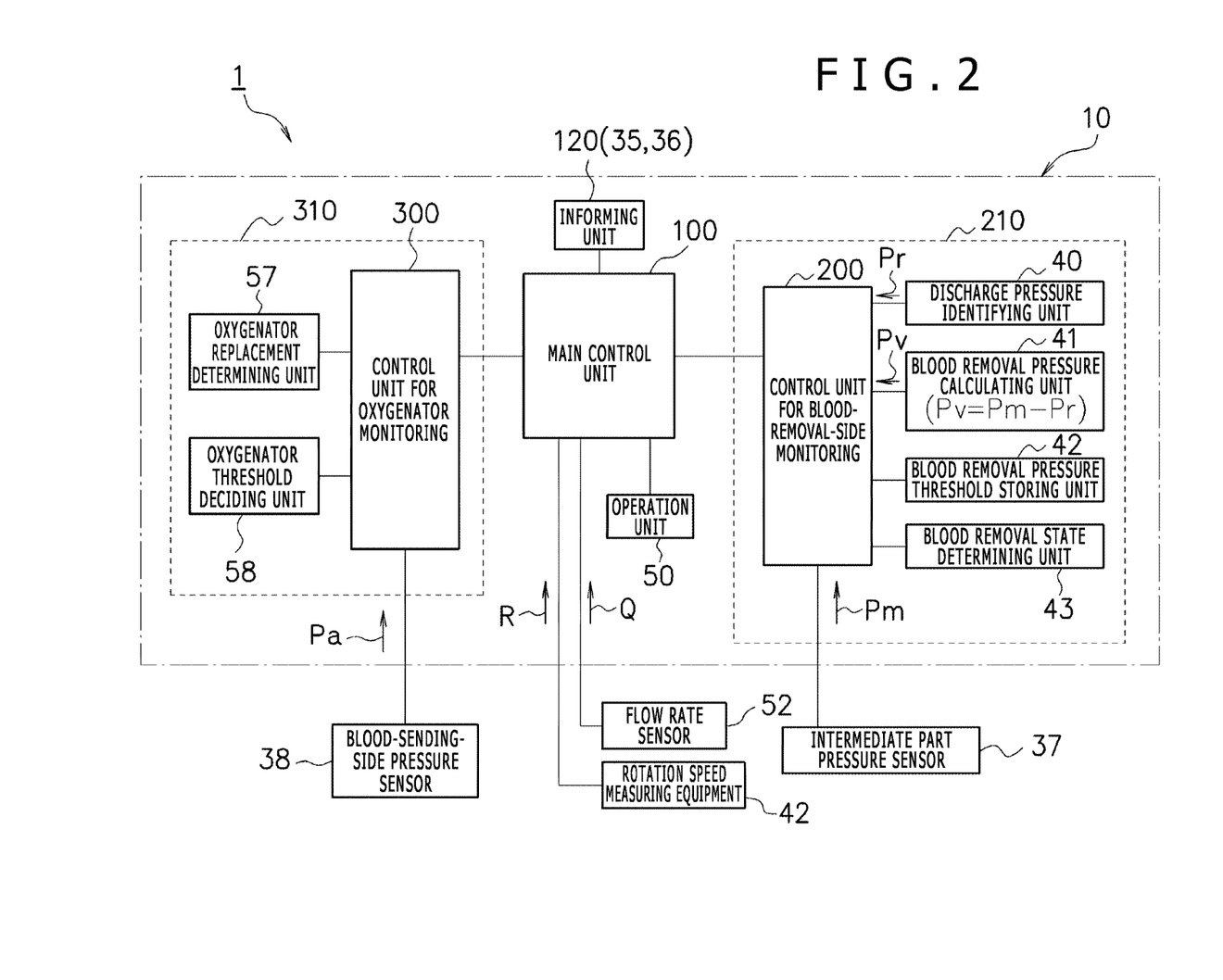
FIG. 2 is a schematic block configuration diagram showing the characteristic configuration of the extracorporeal circulation device of FIG. 1.
Figure 3:
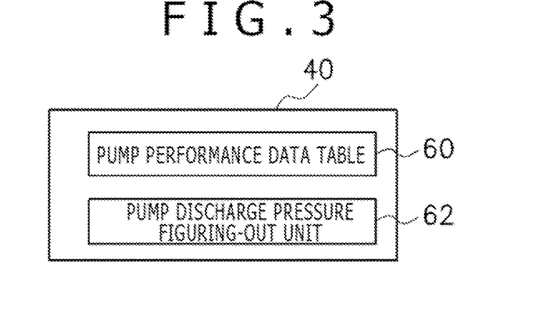
FIG. 3 is a schematic block diagram showing the main configuration of a discharge pressure identifying unit in FIG. 2.
Figure 4:
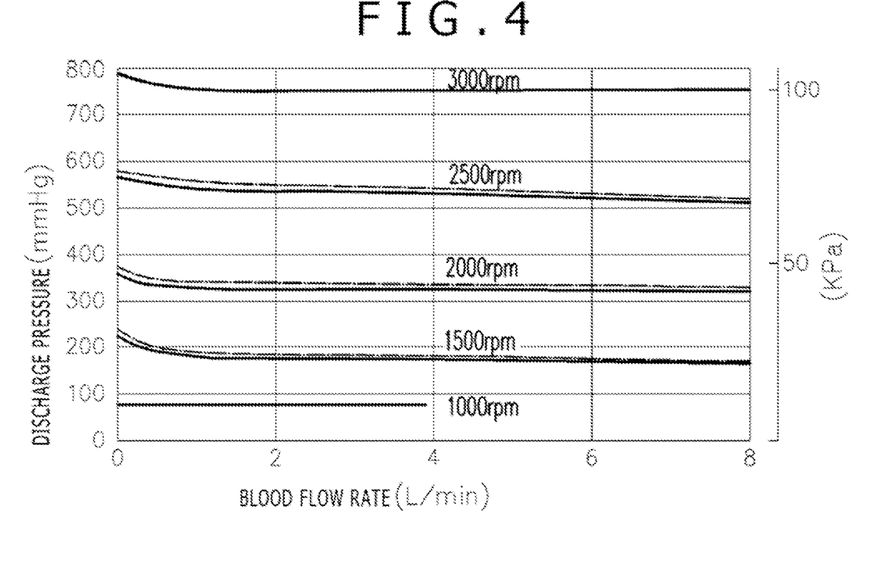
FIG. 4 is performance data showing the correlation among the discharge pressure, the blood flow rate, and the rotation speed regarding a centrifugal pump.
Figure 5:
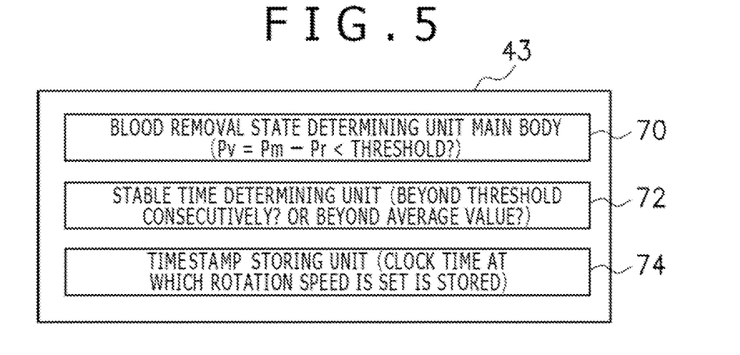
FIG. 5 is a schematic block diagram showing the main configuration of a blood removal state determining unit in FIG. 2.
Figure 6:
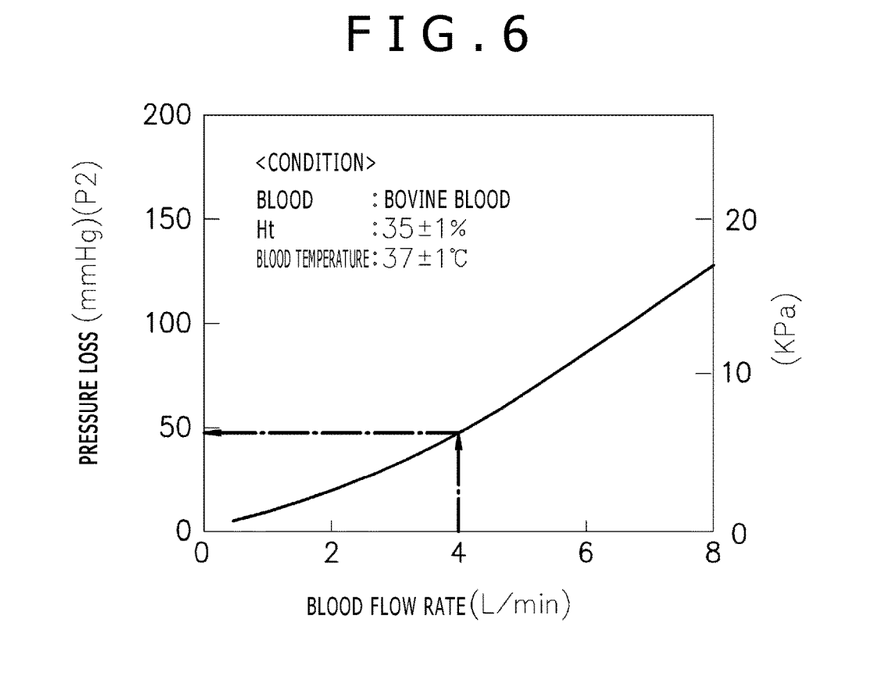
FIG. 6 is performance data showing the correlation between the blood flow rate and the pressure loss regarding an oxygenator.
Figure 7:
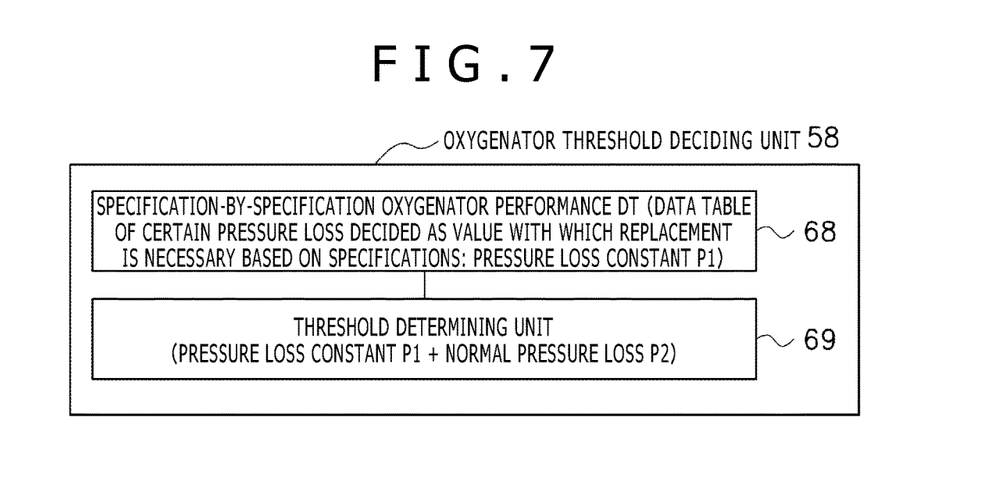
FIG. 7 is a schematic block diagram showing the main configuration of an oxygenator threshold deciding unit in FIG. 2.

Next, the system configuration of the above-described extracorporeal circulation device 1 will be described by reference to FIG. 2 to FIG. 7. FIG. 2 is a schematic block diagram showing the characteristic configuration of the extracorporeal circulation system 1. FIG. 3 is a schematic block diagram showing the main configuration of a discharge pressure identifying unit 40 in FIG. 2. FIG. 4 is performance data showing the correlation among the discharge pressure, the blood flow rate, and the rotation speed regarding the centrifugal pump. FIG. 5 is a schematic block diagram showing the main configuration of a blood removal state determining unit 43 in FIG. 2. FIG. 6 is performance data showing the correlation between the blood flow rate and the pressure loss regarding the oxygenator. FIG. 7 is a schematic block diagram showing the main configuration of an oxygenator threshold deciding unit 58 in FIG. 2.

As shown in FIG. 2, the extracorporeal circulation device 1 has, in the controller 10, a "module 210 for the blood removal line" and a "module 310 for the oxygenator" that are obtained by modularizing the above-described main control unit 100 and programs.

First, the module 210 for the blood removal line will be described. The module 210 for the blood removal line has the control unit 200 for blood-removal-side monitoring that carries out operation and control of the whole of this module and the "discharge pressure identifying unit 40," a "blood removal pressure calculating unit 41," a "blood removal pressure threshold storing unit 42," and the "blood removal state determining unit 43" by which data is transferred and received between these units and this control unit 200 for blood-removal-side monitoring.

The "discharge pressure identifying unit 40" is a program for identifying the discharge pressure specific to the centrifugal pump (discharge pressure value corresponding to predetermined performance data specific to the centrifugal pump used) based on the rotation speed R of the centrifugal pump and a blood flow rate Q detected in the flow rate sensor. Specifically, as shown in FIG. 3, the discharge pressure identifying unit 40 has a "pump performance data table 60" and a "pump discharge pressure figuring-out unit 62" in which a program for figuring out the aforesaid specific discharge pressure is stored. The pump performance data table 60 is a data table based on the specific correlation of "rotation speed—blood flow rate—discharge pressure" defined corresponding to each kind (i.e., a particular preexisting design) of centrifugal pump. In the pump performance data table 60 of the present embodiment, a data table corresponding to plural kinds of centrifugal pumps may be stored. For example, a data table created based on the correlation of "rotation speed (rpm)—blood flow rate (L/minute)—discharge pressure (mmHg)" shown in FIG. 4 is stored. Note that the correlation data shown in FIG. 4 is specific to a "CAPIOX" (trade name) centrifugal pump made by Terumo Corporation.

In order to identify a discharge pressure Pr (see FIG. 2) specific to the centrifugal pump by using the pump performance data table 60, based on the program of the pump discharge pressure figuring-out unit 62, the control unit 200 for blood-removal-side monitoring shown in FIG. 2 acquires data of the "rotation speed R" in the aforesaid correlation from the rotation speed measuring equipment 42 through the main control unit 100 and acquires data of the "blood flow rate Q" from the flow rate sensor 52 through the main control unit 100. The discharge pressure Pr figured out from only the relationship between the rotation speed R and the blood flow rate Q is a numerical value corresponding to the predefined performance data specific to the centrifugal pump used and does not correspond to environmental change. For this reason, there is a possibility that the actual discharge pressure may vary from the estimated discharge pressure Pr. The hematocrit value and the blood temperature are potential causes of the numerical value variation. Therefore, it is preferable to take account of the hematocrit value and the blood temperature and correct the numerical value of the estimated discharge pressure Pr. For example, if FIG. 4 is a correlation diagram of the case in which the hematocrit value is 35±1% and the blood temperature is 37±1° C., when the hematocrit value becomes higher than this value or the blood temperature becomes lower, the viscosity of the blood becomes higher and the discharge pressure becomes higher even with the same rotation speed and flow rate as shown by one-dot-chain lines in FIG. 4 for example. Therefore, it is preferable to correct the discharge pressure. This can be done using known methods to estimate the discharge pressure with higher accuracy.

The "blood removal pressure calculating unit 41" in FIG. 2 is a unit for estimating the magnitude of the pressure in the blood removal line 11 in FIG. 1 and specifically is a program that subtracts the discharge pressure Pr identified in the discharge pressure identifying unit 40 in FIG. 2 from the pressure Pm measured by the intermediate part pressure sensor 37 (Pm−Pr). Specifically, the intermediate part pressure sensor 37 in FIG. 1 actually measures the pressure in the interlock tube 3 immediately subsequent to (immediately downstream of) the centrifugal pump 4. This immediately-subsequent pressure is the pressure obtained by adding the discharge pressure of the centrifugal pump 4 to the pressure in the blood removal line 11 attributed to bloodstream from the vein of the patient P. Therefore, as shown in FIG. 2, an estimated pressure value Pv in the blood removal line (hereinafter, referred to as "estimated blood removal pressure") can be obtained by subtracting the discharge pressure Pr of the centrifugal pump (discharge pressure identified in the discharge pressure identifying unit 40) from the pressure Pm actually measured in the intermediate part pressure sensor 37.

The "blood removal pressure threshold storing unit 42" in FIG. 2 is a criterion evaluation unit that stores a threshold necessary for determining whether or not the estimated blood removal pressure Pv corresponds to a failure of the blood removal function. Note that because normally the inside of the blood removal line is in a negative pressure state, a negative numerical value such as −100 mmHg for example is set as the threshold. This threshold differs depending on the sex, age, and condition of the patient and therefore it is preferable that an adjustable threshold can be set by a user. In the present embodiment, the threshold is stored in the blood removal pressure threshold storing unit 42 via the main control unit 100 and the control unit 200 for blood-removal-side monitoring by operation of the operation unit 50. If at least a value obtained by subtracting approximately 50 mmHg from the present estimated blood removal pressure value Pv is employed as the threshold, it is also possible to detect an abnormal state in which the blood removal is not carried out at all due to occlusion of the tube of the blood removal line or the like.

The "blood removal state determining unit 43" in FIG. 2 is a program that determines whether or not the estimated blood removal pressure Pv by the blood removal pressure calculating unit 41 surpasses the required threshold stored by the blood removal pressure threshold storing unit 42 or, conversely, whether or not the estimated blood removal pressure Pv has fallen below the threshold (e.g., after having previously been above the threshold). If the estimated blood removal pressure Pv falls below the threshold, then a loss in the amount of blood of the subject, an improper insertion of the cannula, or the like, which are a potential cause of blood removal failure, may be detected for example. Specifically, the blood removal state determining unit 43 has a blood removal state determining unit main body 70 as shown in FIG. 5 and the determination is made based on a program (estimated blood removal pressure Pv<threshold) of this main body 70. Note that in the concept of the program of the blood removal state determining unit 43, a concept that the estimated blood removal pressure Pv is multiplied by a minus and whether or not the resulting value has surpassed the threshold is determined is also included.

Furthermore, the blood removal state determining unit 43 has a timestamp storing unit 74 for storing clock times at which the rotation speed of the centrifugal pump is adjusted (e.g., either an initial setting or a subsequent change setting). Specifically, if the rotation speed of the centrifugal pump is adjusted by the operation unit 50 shown in FIG. 2, the main control unit 100 outputs the clock time at which the rotation speed is set (hereinafter, referred to as "timestamp") to the blood removal state determining unit 43 through the control unit 200 for blood-removal-side monitoring and the timestamp storing unit 74 in FIG. 5 records the timestamp. A predetermined time window from this timestamp corresponds to a time delay during which the discharge pressure of the centrifugal pump has not yet reached a stable value. Furthermore, for example, when the rotation speed of the centrifugal pump has been changed and the timestamp storing unit 74 has recorded the timestamp, then for a predetermined delay time of n seconds from the timestamp (i.e., a premeasured amount of time required until the discharge pressure of the centrifugal pump becomes stable, which may be about 10 seconds in the case of the present embodiment), the control unit 200 for blood-removal-side monitoring in FIG. 2 does not carry out the determination of whether or not the estimated blood removal pressure Pv has fallen below the threshold based on the program of the blood removal state determining unit main body 70. The present invention is not limited thereto and the "required time until the discharge pressure becomes stable" may be determined by using another method. For example, preferably, if the rotation speed of the centrifugal pump is initially set, the time until the rotation speed detected in the rotation speed measuring equipment 42 rises from 0 to a set rotation speed (e.g., a rotation speed set by the user with the operation unit) is regarded as the "required time until the discharge pressure of the centrifugal pump becomes stable."

Moreover, as shown in FIG. 5, the blood removal state determining unit 43 has a stable time determining unit 72. The stable time determining unit 72 is a program for establishing a predetermined time after which the discharge pressure of the centrifugal pump should be stable (i.e. after the elapse of n seconds from recording of the timestamp by the clock time storing unit 74) and determining whether or not the determination that the estimated blood removal pressure Pv has fallen below the threshold (or the value obtained by multiplying the estimated blood removal pressure Pv by negative one has surpassed the threshold) has been consecutively made based on the program of the blood removal state determining unit main body 70. In the present embodiment, if it has been consecutively determined that the estimated blood removal pressure Pv has fallen below the threshold, this is indicated by the informing unit 120 in FIG. 2 because of the possibility of blood removal failure. The stable time determining unit 72 of the present invention is not limited to such a configuration and may be a program that determines whether or not the average value of the estimated blood removal pressure Pv in the predetermined time in which the discharge pressure of the centrifugal pump should be stable has fallen below the threshold.

Next, the module 310 for the oxygenator existing in the controller 10 in FIG. 2 will be described. The module 310 for the oxygenator has the control unit 300 for oxygenator monitoring that carries out operation and control of the whole of this module and an "oxygenator replacement determining unit 57" and the "oxygenator threshold deciding unit 58" by which data is transferred and received between these units and this control unit 300 for oxygenator monitoring.

The "oxygenator replacement determining unit 57" is a unit for determining whether or not replacement of the oxygenator 2 shown in FIG. 1 is necessary (based on whether or not a blockage value or pressure loss that is indicative of an impaired oxygenator has been detected), and this determination is made by determining the pressure loss in the blood circuit across the oxygenator 2. Specifically, in the oxygenator 2, the pressure loss becomes larger as a result of clogging with a thrombus in the blood circuit thereof, the deterioration of the porous membrane, or the like due to prolonged use. Thus, the oxygenator replacement determining unit 57 checks whether the actual pressure loss surpasses a required threshold and determines the replacement timing. The oxygenator replacement determining unit 57 shown in FIG. 2 is a program that determines whether or not replacement of the oxygenator is necessary based on the difference between the pressure value measured in the blood-sending-side pressure sensor 38 connected to the downstream side of the oxygenator (hereinafter, referred to as "post-oxygenator pressure Pa") and the pressure value measured in the intermediate part pressure sensor 37 connected to the upstream side of the oxygenator (hereinafter, referred to as "pre-oxygenator pressure Pm"). In the case of the present embodiment, the numerical value based on this difference is the numerical value obtained based on "pre-oxygenator pressure Pm minus post-oxygenator pressure Pa" (i.e., the pressure loss in the blood circuit in the oxygenator 2 is calculated by subtracting the post-oxygenator pressure Pa from the pre-oxygenator pressure Pm in this manner). Furthermore, if this calculated pressure loss value surpasses a threshold maintained by the oxygenator threshold deciding unit 58 in FIG. 2, a command to generate a corresponding indication is issued to the informing unit 120. It suffices for the contents of the indication to convey "replacement-related information of the oxygenator." For example, the numerical value calculated by subtracting the "post-oxygenator pressure Pa" from the "pre-oxygenator pressure Pm" may be turned to a graph or the like and be displayed on the display screen in real time.

The "oxygenator threshold deciding unit 58" in FIG. 2 is a unit that determines the required threshold to serve as the basis of whether or not oxygenator replacement is necessary. As shown in FIG. 7, this oxygenator threshold deciding unit 58 has a specification-by-specification oxygenator performance DT 68 and a threshold determining unit 69. The specification-by-specification oxygenator performance DT 68 is a data table relating to a certain pressure loss (constant, hereinafter referred to as "pressure loss constant") P1 with which replacement is deemed to be necessary based on the manufacturer specifications of a plurality of respective oxygenators. For example, in the case of the hollow fiber oxygenator of the present embodiment, the pressure loss constant is approximately 300 to 500 mmHg. It suffices for this pressure loss constant to be decided in advance based on the manufacturer specifications. Furthermore, for example, the pressure loss constant may be decided based on the pressure loss measured when the oxygenator was replaced in the past (pressure loss when a previously used oxygenator reached a known deteriorated condition).

The threshold determining unit 69 derives the threshold by adding a pressure loss that is normal (hereinafter, referred to as "normal pressure loss") P2 corresponding to the blood flow rate of the oxygenator to the pressure loss constant P1 identified in the specification-by-specification oxygenator performance DT 68. Specifically, for example as shown in FIG. 6, which is performance data of "CAPIOX LX" (trade name) made by Terumo Corporation, the blood flow rate and the pressure loss of the oxygenator have a correlation, and the pressure loss naturally changes when the blood flow rate changes. Such a "normal pressure loss P2" that varies based on the blood flow rate is not attributed to the deterioration of the porous membrane of the oxygenator, clogging with a thrombus, or the like and therefore does not need to be deemed as a reason for oxygenator replacement. Therefore, the threshold is derived by adding the "normal pressure loss P2" to the "pressure loss constant P1." This can prevent unnecessary replacement of the oxygenator and avoid the fear of imposing an extra physical burden on the body of the subject. Data of the blood flow rate for identifying the normal pressure loss P2 is distributed in real time from the main control unit 100 connected to the flow rate sensor 52 as shown in FIG. 2. Furthermore, it is preferable that data from which the correlation between the blood flow rate and the normal pressure loss P2 is understood like that shown in FIG. 6 be prepared as a data table for each of the kinds of oxygenators stored in the specification-by-specification oxygenator performance DT 68 in FIG. 7. The threshold for oxygenator replacement is derived in this manner. To cite one example, if the oxygenator is "CAPIOX LX" (trade name) made by Terumo Corporation and the blood flow rate is 4 L/minute, the normal pressure loss P2, which is not attributed to clogging or the like, is approximately 50 mmHg as shown in FIG. 6, and the threshold determining unit 69 in FIG. 7 decides 400 mmHg obtained by adding 50 mmHg (normal pressure loss P2) to 350 mmHg (pressure loss constant P1) as the threshold.

[Operation Example of Extracorporeal Circulation Device]

Figure 8:
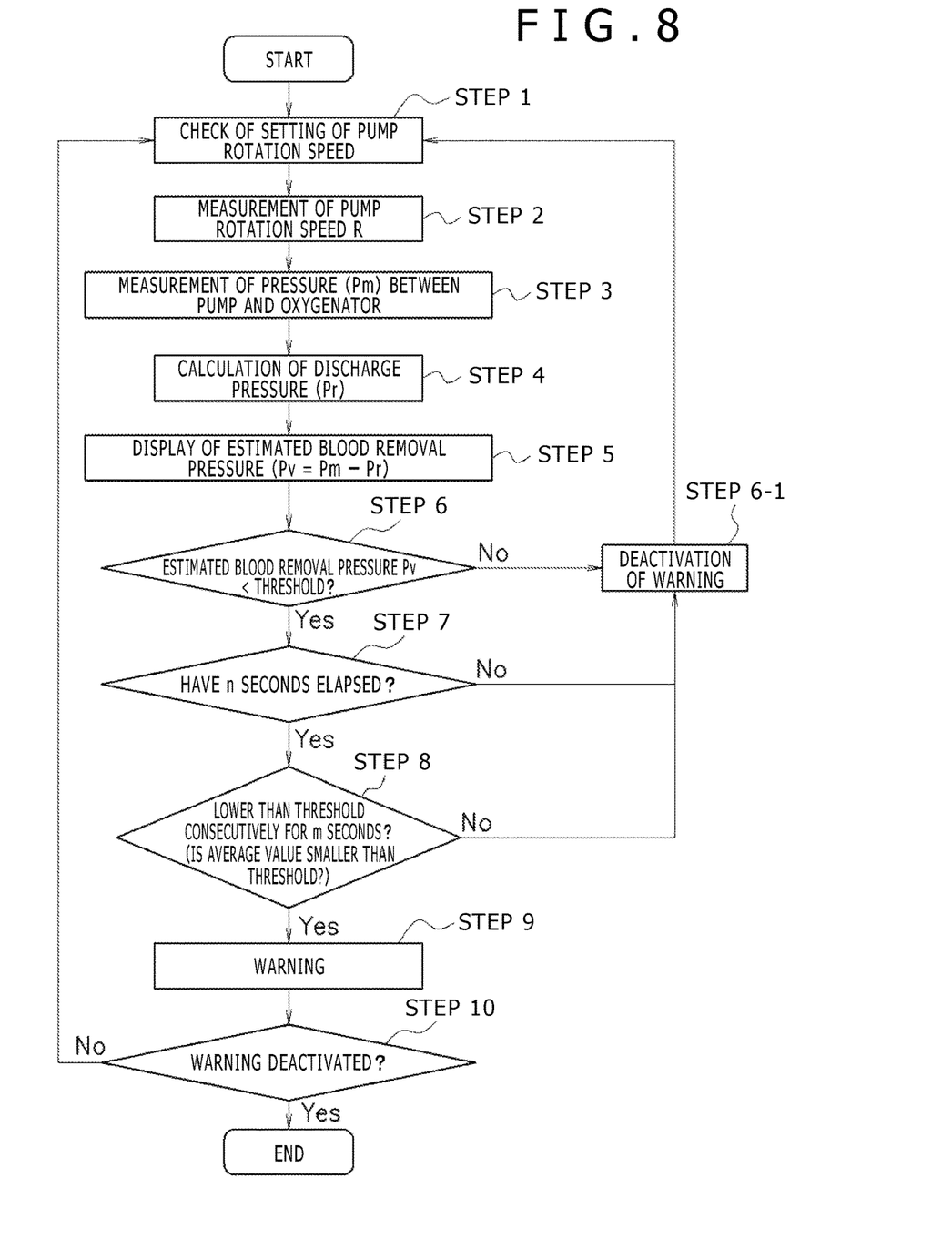
FIG. 8 is a flowchart showing characteristic operation relating to informing of the state of the blood removal side of the extracorporeal circulation device of FIG. 1.

Next, an operation example of the extracorporeal circulation system of the present embodiment will be described. First, operation centered on the module 210 for the blood removal line in FIG. 2 will be described by mainly using the above-described FIG. 2 and FIG. 8. FIG. 8 is a schematic flowchart showing characteristic operation relating to informing of the state of the blood removal side of the extracorporeal circulation device 1 of FIG. 1.

Regarding the extracorporeal circulation device of the present embodiment, blood circulation is started after the power supply of the controller 10 shown in FIG. 2 is turned on and thereafter initial setting is carried out by using the operation unit 50 and so forth as preparation prior to the blood circulation. As part of the initial setup, selection of the kinds of the oxygenator and the centrifugal pump exists (e.g., according to a manufacturer and model number). In the present embodiment, these kinds can be automatically input by reading the barcodes BC displayed on the oxygenator 2 and the centrifugal pump 4 shown in FIG. 1 by the barcode reader 81. The present invention is not limited thereto and the model numbers of the oxygenator and the centrifugal pump may be selected and input with a pull-down menu for example. Furthermore, as part of the initial setup, a selection of the rotation speed of the centrifugal pump is made. When this setting is carried out, as shown in FIG. 8, the setting (including also subsequent changes to the setting) of the rotation speed of the centrifugal pump is checked (step 1) and a corresponding timestamp is recorded in the timestamp storing unit 74 in FIG. 5. Moreover, as part of the initial setup, the threshold relating to the pressure of the blood removal line serving as the determination criterion of blood removal failure also exists. The threshold is decided by the operation unit 50 in FIG. 2 according to the sex, age, and condition of the patient.

Subsequently, the rotation speed of the centrifugal pump is measured in the rotation speed measuring equipment 42 in FIG. 2 (step 2 in FIG. 8). This measured numerical value is sequentially sent to the module 210 for the blood removal line in FIG. 2 and is updated and recorded in a storing unit, which is not diagrammatically represented. Next, the pressure value between the centrifugal pump and the oxygenator (pressure Pm of the immediately-downstream side of the centrifugal pump) is measured in the intermediate part pressure sensor 37 in FIG. 2 (step 3 in FIG. 8). Note that in the present invention, the order of step 2 and step 3 in FIG. 8 may be reversed. Subsequently, the discharge pressure Pr specific to the centrifugal pump is identified (step 4 in FIG. 8). Specifically, the blood flow rate Q of the blood sending line is measured in the flow rate sensor 52 in FIG. 2 and the rotation speed R of the centrifugal pump already measured in step 2 is used to identify the discharge pressure Pr of the centrifugal pump based on the correlation of "blood flow rate—rotation speed—discharge pressure" specific to the centrifugal pump used, like that shown in FIG. 4 for example. At this time, it is more preferable to identify the discharge pressure Pr with taking account of the hematocrit value and the blood temperature. Note that in the present invention, the order of step 3 and step 4 in FIG. 8 may be reversed.

Next, the discharge pressure Pr of the centrifugal pump identified in step 4 is subtracted from the pressure Pm measured in step 3 in FIG. 8 (pressure measured in the intermediate part pressure sensor) to calculate the estimated blood removal pressure Pv, and the pressure value is displayed on the display screen 35 in FIG. 1 (step 5 in FIG. 8). This operation from step 2 to step 5 is carried out at all times and the estimated blood removal pressure Pv can be displayed in real time.

Subsequently, it is determined whether or not the estimated blood removal pressure Pv calculated in step 5 in FIG. 8 falls below the required threshold (step 6). Note that this determination is carried out by the blood removal state determining unit 43 in FIG. 2. Furthermore, the required threshold is a threshold set in advance by the user at the time of initial setup. If the estimated blood removal pressure Pv surpasses the required threshold in step 6 in FIG. 8, warning is not issued (step 6-1) and the process returns to step 1, so that the operation is started from the check of setting of the rotation speed of the centrifugal pump. In contrast, if it is determined that the estimated blood removal pressure Pv has fallen below the required threshold in step 6 in FIG. 8, it is determined whether or not the required time for stabilization of the discharge pressure (n seconds) has elapsed from the timestamp (including also changes of setting) of the rotation speed of the centrifugal pump checked in step 1 (step 7). It suffices for this required time to be identified according to the characteristics of the drive motor. For example, in the case of "CAPIOX (trade name) centrifugal pump controller SP-101 (drive motor): made by Terumo Corporation," it is sufficient to set the required time to approximately 10 seconds.

Then, if it is determined that the required time until the discharge pressure becomes stable (n seconds) has not elapsed in step 7 in FIG. 8, although the estimated blood removal pressure Pv has fallen below the threshold, it can be envisaged that this is a phenomenon accompanying changing of the centrifugal pump rotation speed. Thus, warning is not carried out (step 6-1) and the process returns to step 1, so that the operation is started from the check of setting of the rotation speed of the centrifugal pump. In contrast, the process proceeds to step 8 if it is determined that the n seconds have elapsed in step 7. Then, it is determined whether or not the estimated blood removal pressure Pv has consecutively fallen below the required threshold in a predetermined time in which the discharge pressure of the centrifugal pump should be stable (m seconds), based on the program of the stable time determining unit 72 in FIG. 5. The purpose of determining whether or not the estimated blood removal pressure Pv has not surpassed the threshold consecutively for the m seconds in step 8 in FIG. 8 is to exclude warning due to pressure variation of instantaneous bending of the tube or the like. Therefore, it is preferable for these m seconds to be short compared with the n seconds until the discharge pressure of the centrifugal pump becomes stable in step 7. Specifically, the m seconds are the number of seconds that is equal to or longer than the number of seconds with which it can be determined that the estimated blood removal pressure Pv gets beyond the threshold plural times, and is shorter than the n seconds in step 7. Preferably, the m seconds are equal to or shorter than half the n seconds in step 7 (in the present embodiment, equal to or shorter than 5 seconds). If it is determined that the estimated blood removal pressure Pv has not consecutively fallen below the threshold as a result, warning is not carried out (step 6-1) and the process returns to step 1. On the other hand, if it is determined that the estimated blood removal pressure Pv has fallen below the required threshold consecutively for the m seconds, the process proceeds to step 9, where display of "blood removal failure" or the like is carried out and warning is issued by the alarm to inform the user of the existence of possibility of blood removal failure.

Although the determination of whether or not the estimated blood removal pressure Pv has fallen below the required threshold consecutively for the m seconds is carried out in step 8 in FIG. 8, whether or not the average value of the estimated blood removal pressure Pv in the m seconds has fallen below the threshold may be employed as the determination criterion. Then, after the warning is issued in step 9, deactivation of the warning is checked (step 10). If the warning is deactivated, the process is ended. In contrast, if the warning is not deactivated in step 10, the process returns to step 1 and the monitoring of the blood removal failure is continued in a similar manner.

Figure 9:
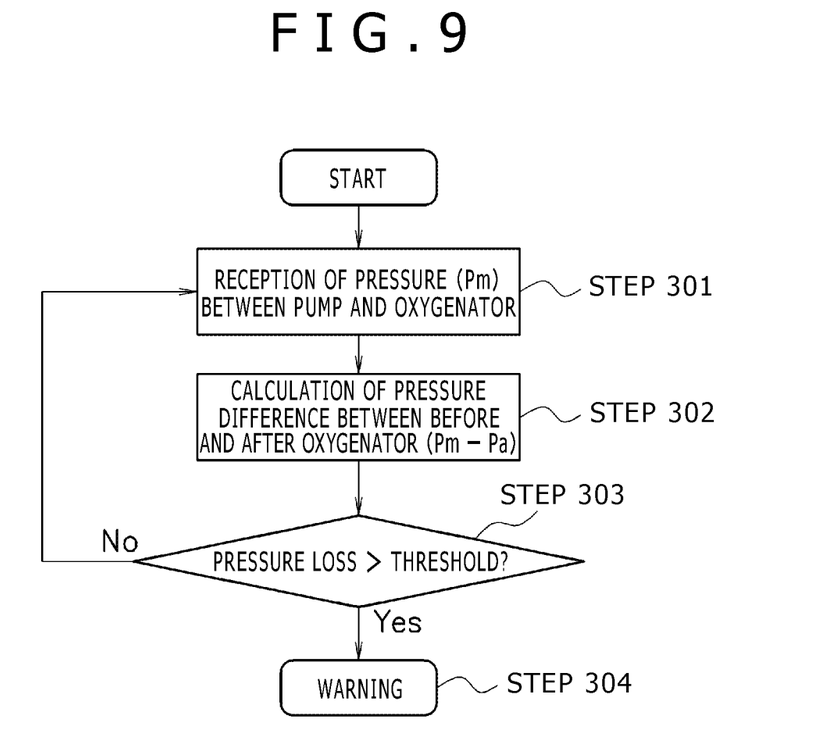
FIG. 9 is a flowchart showing characteristic operation relating to informing of oxygenator replacement of the extracorporeal circulation system of FIG. 1.

Next, operation centered on the module 310 for the oxygenator in FIG. 2 will be described by mainly using the above-described FIG. 2 and FIG. 9. FIG. 9 is a schematic flowchart showing characteristic operation relating to informing of oxygenator replacement of the extracorporeal circulation device 1 of FIG. 1. In this extracorporeal circulation device, when the pressure Pm between the centrifugal pump and the oxygenator is measured in step 3 in FIG. 8 (when the intermediate part pressure sensor 37 in FIG. 2 measures the pressure value Pm), the module 210 for the blood removal line shown in FIG. 2 transmits the pressure value Pm to the module 310 for the oxygenator through the main control unit 100 and the control unit 300 for oxygenator monitoring receives it (step 301 in FIG. 9).

Subsequently, the process proceeds to step 302 in FIG. 9 and the pressure difference between before and after the oxygenator is calculated. Specifically, the pressure (pre-oxygenator pressure) Pm received in step 301 is subtracted from the pressure (post-oxygenator pressure) Pa measured in the blood-sending-side pressure sensor 38 in FIG. 2 to estimate the pressure loss in the blood circuit of the oxygenator. Next, it is determined whether or not the pressure loss calculated in step 302 surpasses the required threshold (step 303). The threshold in this step 303 is a threshold obtained from the threshold determining unit 69 in FIG. 7 and is the numerical value obtained by adding the normal pressure loss P2, which corresponds to the blood flow rate of the oxygenator (which is not attributed to clogging with a thrombus or the like), to the pressure loss constant P1 identified through the operation unit or barcode reading at the time of initial setting. Then, if the calculated pressure loss does not surpass the required threshold, the process returns to step 301. In contrast, if the pressure loss surpasses the required threshold, it is determined that replacement of the oxygenator is necessary and display of "oxygenator replacement" is carried out on the display screen 35 in FIG. 1. In addition, warning is made by the alarm 36 (step 304 in FIG. 9). The warning sound at the time and the warning sound in step 8 in FIG. 8 may be the same because a check by the display screen is possible, or may be different.

The present invention is not limited to the aforesaid embodiment and various changes can be made in such a range as not to depart from the scope of claims. For example, in the aforesaid embodiment, the extracorporeal circulation system that can deal with various oxygenators and centrifugal pumps is employed. However, the extracorporeal circulation system may be compatible with only one kind of oxygenator and centrifugal pump decided in advance. This eliminates the need to select the kinds of oxygenator and blood pump in initial setup. Furthermore, the module 210 for the blood removal line and the module 310 for the oxygenator in FIG. 2 are configured by modularizing programs. However, they may be configured by hardware circuits. In addition, in the present invention, as the configuration for determining replacement of the oxygenator, it is determined that the replacement of the oxygenator is necessary if the numerical value obtained by subtracting the post-oxygenator pressure Pa from the pre-oxygenator pressure Pm surpasses the required threshold in FIG. 9. However, for example, it may be determined that the replacement of the oxygenator is necessary if the ratio between the pre-oxygenator pressure Pm and the post-oxygenator pressure Pa surpasses a required threshold. Moreover, in the present invention, the module 310 for the oxygenator and the blood-sending-side pressure sensor 38, which are shown in FIG. 2, for determining replacement of the oxygenator and the operation example of FIG. 9 are not essential constituent elements.

What is claimed is:

1. An extracorporeal circulation system comprising:
   a blood removal line to withdraw blood from inside a body of a subject;
   a centrifugal pump connected downstream of the blood removal line and operating at a set speed;
   speed measuring equipment associated with the centrifugal pump to detect a rotation speed of the centrifugal pump;
   an oxygenator connected downstream relative to the centrifugal pump via an intermediate tube;
   a blood sending line downstream relative to the oxygenator to return blood to the body;
   a flow rate sensor to detect a blood flow rate in the blood sending line;
   an intermediate part pressure sensor to detect pressure in the intermediate tube between the centrifugal pump and the oxygenator;
   a discharge pressure identifying unit programmed with a predetermined correlation between a pump discharge pressure, a pump flow rate, and a pump rotation speed, wherein the predetermined correlation is specific to a particular preexisting design of the centrifugal pump, and wherein the discharge pressure identifying unit is programmed to identify a corresponding discharge pressure according to the detected rotation speed of the centrifugal pump and the blood flow rate detected in the flow rate sensor; and a blood removal pressure calculating unit programmed to subtract the discharge pressure identified in the discharge pressure identifying unit from the pressure measured by the intermediate part pressure sensor to estimate pressure in the blood removal line.

2. The extracorporeal circulation system according to claim 1, further comprising:

a blood removal state determining unit programmed to determine whether or not the pressure calculated in the blood removal pressure calculating unit has surpassed a predetermined threshold; and informing means programmed to indicate whether the blood removal state determining unit has determined that the pressure calculated in the blood removal pressure calculating unit has surpassed or fallen below the threshold.

3. The extracorporeal circulation system according to claim 2, wherein the blood removal state determining unit is programmed to carry out the determination only after determining that the discharge pressure of the centrifugal pump has become stable after the set speed of the centrifugal pump is changed.

4. The extracorporeal circulation system according to claim 2, wherein the blood removal state determining unit is programmed to determine whether or not an average value of the pressure calculated in the blood removal pressure calculating unit remains above the threshold for a predetermined time before the informing means provides the indication.

5. An extracorporeal circulation system comprising:
a blood removal line to withdraw blood from inside a body of a subject;
a centrifugal pump connected downstream of the blood removal line and operating at a set speed;
speed measuring equipment associated with the centrifugal pump to detect a rotation speed of the centrifugal pump;
an oxygenator connected downstream relative to the centrifugal pump via an intermediate tube;
a blood sending line downstream relative to the oxygenator to return blood to the body;
a flow rate sensor to detect a blood flow rate in the blood sending line;
an intermediate part pressure sensor to detect pressure in the intermediate tube between the centrifugal pump and the oxygenator; and
a blood removal pressure determining unit programmed to determine a pressure in the blood removal line in response to a difference between 1) a pump discharge value from a pump performance data table stored in advance according to a predetermined correlation specific to a particular preexisting design of the centrifugal pump between discharge pressure, pump flow rate, and pump rotation speed, wherein the pump discharge value is identified in the pump performance data table using the detected rotation speed and the detected blood flow rate, and 2) the pressure measured by the intermediate part pressure sensor.

6. The extracorporeal circulation system according to claim 1, further comprising a guard member that engages the intermediate tube to keep the intermediate tube straight.

* * * * *